(12) United States Patent
Koike et al.

(10) Patent No.: US 7,857,863 B2
(45) Date of Patent: Dec. 28, 2010

(54) ONE-PART HAIR DYE COMPOSITION

(75) Inventors: Kenzo Koike, Tokyo (JP); Atsuko Ebato, Tokyo (JP)

(73) Assignee: Kao Corporation, Tokyo (JP)

( * ) Notice: Subject to any disclaimer, the term of this patent is extended or adjusted under 35 U.S.C. 154(b) by 90 days.

(21) Appl. No.: 12/303,610

(22) PCT Filed: Jun. 7, 2007

(86) PCT No.: PCT/JP2007/000614
§ 371 (c)(1),
(2), (4) Date: Dec. 5, 2008

(87) PCT Pub. No.: WO2007/141920
PCT Pub. Date: Dec. 13, 2007

(65) Prior Publication Data
US 2010/0170048 A1    Jul. 8, 2010

(30) Foreign Application Priority Data

| Jun. 7, 2006 | (JP) | ............................. 2006-158942 |
| Jun. 7, 2006 | (JP) | ............................. 2006-158943 |
| Jun. 7, 2006 | (JP) | ............................. 2006-159010 |
| Jun. 7, 2006 | (JP) | ............................. 2006-159129 |
| Jun. 7, 2006 | (JP) | ............................. 2006-159148 |

(51) Int. Cl.
*A61Q 5/10* (2006.01)
(52) U.S. Cl. .................... 8/405; 8/435; 8/552; 8/574; 8/594; 8/604; 8/606; 8/611; 8/670
(58) Field of Classification Search .................... 8/405, 8/435, 552, 574, 594, 604, 606, 611, 670
See application file for complete search history.

(56) References Cited

U.S. PATENT DOCUMENTS

| 4,208,183 | A | 6/1980 | Grollier et al. |
| 4,900,326 | A | 2/1990 | Grollier |
| 5,021,067 | A | 6/1991 | Grollier |
| 5,704,949 | A | 1/1998 | Prota et al. |
| 2004/0019982 | A1 | 2/2004 | Pratt et al. |
| 2006/0000032 | A1* | 1/2006 | Knuebel et al. ................. 8/405 |

FOREIGN PATENT DOCUMENTS

| CN | 1599590 A | 3/2005 |
| DE | 10120915 A1 | 11/2001 |
| EP | 0 533 937 A1 | 3/1993 |
| EP | 1 254 650 A2 | 11/2002 |
| EP | 1 430 873 A1 | 6/2004 |
| EP | 1433470 A1 | 6/2004 |
| JP | 57-192310 A | 11/1982 |
| JP | 8-32618 | 3/1996 |
| JP | 11-12139 | 1/1999 |
| JP | 2002-322038 A | 11/2002 |
| JP | 2003-055175 | 2/2003 |
| JP | 2003-342139 A | 12/2003 |

| WO | WO 92/14441 A1 | 9/1992 |
| WO | WO 99/66890 A1 | 12/1999 |
| WO | WO 2004/024109 A1 | 3/2004 |

OTHER PUBLICATIONS

Patent Abstracts of Japan, English language abstract of JP 57-192310, Nov. 26, 1982 (listed on accompanying PTO/SB/08A as document FP1).
Dialog Database, Derwent World Patent Index File 351 Accession No. 6077403, English language abstract for WO 1992/014441 A1, published Sep. 3, 1992 (listed on accompanying PTO/SB/08A as document FP2).
Dialog Database, Derwent World Patent Index File 351 Accession No. 10376798, English language abstract for WO 1999/066890 A1, published Dec. 29, 1999 (listed on accompanying PTO/SB/08A as document FP4).
Dialog Database, Derwent Accession No. 2002-076390/200211, English language abstract for DE 10120915 A1, Nov. 15, 2001 (listed on accompanying PTO/SB/08A as document FP5).
Dialog Database, Derwent World Patent Index File 351 Accession no. 14485871, English language abstract for WO 2004/024109 A1 (listed on accompanying PTO/SB/08A as document FP7).
Dialog Database, Derwent Accession No. 2004-490110/200447, English language abstract for EP 1433470 A1, Jun. 20, 2004 (listed on accompanying PTO/SB/08A as document FP8).
International Search Report for International Application No. PCT/JP2007/000614, mailed on Jul. 10, 2007, Japanese Patent Office, Tokyo, Japan.
Koike et al., U.S. Appl. No. 12/303,604 (Natl. Phase of PCT/JP2007/000612; Int'l Filing Date: Jun. 7, 2007).
Koike et al., U.S. Appl. No. 12/303,607 (Natl. Phase of PCT/JP2007/000613; Int'l Filing Date: Jun. 7, 2007).
Dialog Database, Derwent World Patent Index File 351 Accession No. 4239691, English language abstract for JP 08-32618 (JP 1996032618), published Mar. 29, 1996 (listed on accompanying PTO/SB/08A as document FP9).
International Preliminary Report on Patentability issued Jan. 13, 2009, with the English language translation of the Written Opinion for PCT/JP2007/000614, filed Jun. 7, 2007, The International Bureau of WIPO, Geneva, Switzerland.
Dialog Database, Derwent World Patent Index File 351 Accession No. 7453523, English language abstract for JP-A-2002-322038 A, published Nov. 8, 2002.
Dialog Database, Derwent World Patent Index File 351 Accession No. 14034115, English language abstract for JP-A-2003-342139 A, published Dec. 3, 2003.
USPTO Office action for U.S. Appl. No. 12/303,604 dated Mar. 10, 2010, and reply thereto filed Aug. 18, 2010.

(Continued)

*Primary Examiner*—Eisa B Elhilo
(74) *Attorney, Agent, or Firm*—Sterne, Kessler, Goldstein & Fox P.L.L.C.

(57) ABSTRACT

Provided are a one-part hair dye composition containing (A) a combination of 5,6-dihydroxyindole and 5,6-dihydroxyindole-2-carboxylic acid, (B) either one of (b1) ascorbic acid or salt thereof or (b2) sulfurous acid or salt thereof, and (C) an alkali agent and having a pH of from 8 to 11; and a method of selecting the kind of Component (B), thereby controlling a hair color upon dyeing the hair.

13 Claims, No Drawings

OTHER PUBLICATIONS

USPTO Office action for U.S. Appl. No. 12/303,607 dated Apr. 5, 2010, and reply thereto filed Aug. 18, 2010.

Dialog World Patent Index File 351 Accession No. 9688038, English language abstract and family members for JP11-12139, published Jan. 19, 1999.

International Preliminary Report on Patentability including the Written Opinion for PCT/JP2007/000612 (the PCT phase of U.S. Appl. No. 12/303,604), issued Jan. 13, 2009 by the International Bureau of WIPO, Geneva, Switzerland.

International Preliminary Report on Patentability including the Written Opinion for PCT/JP2007/000613 (the PCT phase of U.S. Appl. No. 12/303,607), issued Jan. 13, 2009 by the International Bureau of WIPO, Geneva, Switzerland.

Office action for CN 200780020625.2 (which corresponds to U.S. Appl. No. 12/303,607), mailed Jul. 16, 2010 from the Patent Office of the People's Republic of China, Beijing, China.

\* cited by examiner

ONE-PART HAIR DYE COMPOSITION

FIELD OF THE INVENTION

The present invention relates to a one-part hair dye composition capable of dyeing hair into different hair colors without using a coupler.

BACKGROUND OF THE INVENTION

Air-oxidative hair dye compositions using a melanin precursor such as indoles or indolines have conventionally been known (refer to, for example, Patent Documents 1 to 3). These hair dyes however require use of a coupler in combination with a melanin precursor in order to change the color of hair dyed with them.

Patent Document 1 JP-B-8-32618
Patent Document 2 JP-A-2003-55175
Patent Document 3 JP-A-2002-322038

DISCLOSURE OF THE INVENTION

In one aspect of the present invention, there is provided a one-part hair dye composition, having a pH of from 8 to 11, containing the following components (A) to (C):

(A) a combination of 5,6-dihydroxyindole and 5,6-dihydroxyindole-2-carboxylic acid, (B) either one of (b1) ascorbic acid or salt thereof or (b2) sulfurous acid or salt thereof, and (C) an alkali agent.

In another aspect of the present invention, there is also provided a method of controlling the color of hair dyed with the composition by selecting either one of (b1) or (b2) as Component (B) of the above-described one-part hair dye composition.

MODE FOR CARRYING OUT THE INVENTION

The present invention relates to an air-oxidative hair dye composition capable of dying hair into different colors without using a coupler.

The present inventors have found that the above-described problem of an air oxidative hair dye composition using a melanin precursor can be overcome by using in combination two specific compounds as the melanin precursor and at the same time using either one of two specific anti-oxidants and an alkali agent.

It is possible to dye hair into a natural color and in addition, control the final hair color by using, as the melanin precursor of Component (A), 5,6-dihydroxyindole and 5,6-dihydroxyindole-2-carboxylic acid. A molar ratio of 5,6-dihydroxyindole to 5,6-dihydroxyindole-2-carboxylic acid is adjusted preferably within a range of from 50:50 to 999:1, more preferably from 80:20 to 99:1. Amounts of 5,6-hydroxyindole and 5,6-dihydroxyindole-2-carboxylic acid can be determined by reversed phase HPLC.

The total content of the compounds as Component (A) in the hair dye composition of the present invention is preferably from 0.05 to 5 wt. %, more preferably from 0.1 to 2 wt. % from the viewpoints of dyeing properties and stability.

As the antioxidant as Component (B), either one of (b1) ascorbic acid or salt thereof or (b2) sulfurous acid or salt thereof is used. The salt of ascorbic acid or sulfurous acid is, for example, a sodium salt. When (b1) is used, hair dyed with the resulting composition acquires a reddish brown color, while when (b2) is used, hair acquires a bluish dark gray color.

The content of Component (B) in the hair dye composition of the present invention is preferably from 0.01 to 5 wt. %, more preferably from 0.05 to 2 wt. %, even more preferably from 0.1 to 1 wt. % from the viewpoints of dyeing properties and control of the color tone.

As the alkali agent as Component (C), alkali agents typically employed for hair dyes can be added. Examples include aqueous ammonia, alkanolamines such as mono-, di- or triethanolamine; alkyl- or aralkylamines such as butylamine and benzylamine; basic amino acids such as arginine, lysine and histidine; inorganic bases such as sodium hydroxide, potassium hydroxide, sodium carbonate and potassium carbonate; and guanidine carbonate and amino acids. Of these, monoethanolamine is preferred from the viewpoint of its dyeing power.

These alkali agents as Component (C) may be used either singly or in combination of two or more. Their content in the hair dye composition of the present invention is preferably from 0.01 to 20 wt. %, more preferably from 0.1 to 10 wt. % from the viewpoint of dyeing properties.

In the hair dye composition of the present invention, a thickening polymer may be incorporated further from the viewpoints of usability, coating properties and adhesion. The thickening polymer may be either a nonionic or ionic polymer. Examples of the nonionic thickening polymer include polysaccharide polymers such as hydroxyethyl cellulose (for example, "SE-850", product of Daicel Chemical and "Cellosize HECQP52000H", product of Nagase Co.), sodium carboxymethylcellulose (for example, "CMC Daicel 1220", product of Daicel Chemical), sodium hydroxyethylcellulose hydroxypropyl stearyl ether hydroxypropylsulfonate (for example, a compound described in Preparation Example 1 of JP-A-11-12139), hydroxypropylmethyl cellulose (for example, "Metolose 60SH-10000", product of Shin-Etsu Chemical), guar gum (for example, "Fiberon S", product of Dainippon Sumitomo Pharma), pullulan (for example, "Pullulan PI-20", product of Hayashibara Inc.), hydroxypropyl chitosan (for example, "Chitofilmer HV-10", product of Ichimaru Pharcos), and chitosan•dl-pyrrolidonecarboxylate (for example, "Chitomer PC", product of Union Carbide); and other polymers such as polyvinylpyrrolidone ("Luviskol K-12", "Luviskol K-30", and "PVP K-120", each product of BASF), polyvinyl alcohol ("Gohsenol EG-40", product of Nippon Synthetic Chemical Industry), vinyl alcohol/vinylamine copolymer ("VA-120-HCl", product of Air Products and Chemicals), and high polymerization degree polyethylene glycol ("Polyox WSRN-60K", product of Union Carbide/Japan).

Examples of the anionic thickening polymers include polysaccharide polymers such as carrageenan (for example, "Soageena LX22" and "Soageena ML210", each product of Mitsubishi Rayon), xanthan gum (for example, "Echo gum T", product of Dainippon Sumitomo Pharma), welan gum (for example, "K1C376" and "K1A96", each product of Sansho), and hydroxypropyl xanthan gum (for example, "Rhaball gum EX", product of Dainippon Sumitomo Pharma); and other anionic thickening polymers such as polyacrylic acid ("Carbopol 941" and "Carbopol 981", each product of Noveon), acrylic acid/alkyl methacrylate copolymer ("Carbopol ETD2020", product of Noveon), and hydrolysate of a lower alkyl vinyl ether/maleic anhydride copolymer partially crosslinked with a terminal-unsaturated diene compound or monoalkyl ester thereof ("Stabilize 06" and "Stabilize QM", each product of ISP).

As the cationic thickening polymers, those having, in the side chain of the polymer chain thereof, an amino group or ammonium group or those containing a diallyl quaternary ammonium salt as a constituent unit, each in the form of an aqueous solution, are usable. Examples of them include polysaccharide polymers such as a cationic cellulose derivative (for example, "Reoguard G" and "Reoguard GP", each product of Lion Corporation, "Polymer JR-125", "Polymer JR-400", "Polymer JR-30M", "Polymer LR-400", and "Polymer LR-30M", each product of Union Carbide, and "Celquat H-100" and "Celquat L-200", each product of National Starch & Chemical), and a cationic guar gum derivative (for example, "Juguar C-13S" and "Juguar C-17", each product of Rhodia, and "Rhaball Gum CG-M", "Rhaball Gum CG-M7", and "Rhaball CG-M8M", each product of Dainippon Sumitomo Pharma); and other cationic thickening polymers such as polymer or copolymer of a diallyl quaternary ammonium salt ("Merquat 100", "Merquat 280", "Merquat 295", and "Merquat 550", each, product of Calgon), and a quaternized polyvinylpyrrolidone derivative ("Gafquat 734", "Gafquat 755" and "Gafquat 755N", each product of ISP Japan).

Of these polymers, polysaccharide thickening polymers are preferred, with natural polymers having a cellulose skeleton or xanthan gum skeleton being more preferred. These thickening polymers may be used either singly or in combination of two or more. The content of the thickening polymer(s) in the hair dye composition of the present invention is preferably from 0.05 to 10 wt. %, more preferably from 0.1 to 7 wt. %, even more preferably from 0.1 to 5 wt. %, even more preferably from 0.1 to 3 wt. %, even more preferably from 0.2 to 3 wt. % from the viewpoints of usability and coating properties. The hair dye composition of the present invention has a viscosity of preferably from 100 to 8000 mPa·s, more preferably from 300 to 5000 mPa·s from the viewpoints of coating properties and reduced dripping. The term "viscosity" as used herein is a value determined after rotation of the composition for 1 minute at 6 rpm at 25° C. by a Brookfield viscometer.

In the hair dye composition of the present invention, an aromatic alcohol may be incorporated further in order to improve the dyeing properties. Examples of the aromatic alcohol include benzyloxyethanol, benzyl alcohol, phenethyl alcohol, γ-phenylpropyl alcohol, cinnamic alcohol, anisyl alcohol, p-methylbenzyl alcohol, α,α-dimethylphenethyl alcohol, α-phenylethanol, and phenoxyethanol. Of these, benzyloxyethanol and benzyl alcohol are preferred.

The above-described aromatic alcohols may be used either singly or in combination of two or more. The content of the aromatic alcohol(s) in the hair dye composition of the present invention is preferably from 0.01 to 10 wt. %, more preferably from 0.5 to 5 wt. % from the viewpoints of improvement in dyeing properties and coating properties.

In the hair dye composition of the present invention, a surfactant may be incorporated further in order to improve foaming properties and coating properties. Any one of non-ionic surfactants, anionic surfactants, cationic surfactants and amphoteric surfactants may be used as such a surfactant.

Examples of the nonionic surfactant include polyoxyalkylene alkyl ethers, polyoxyalkylene alkenyl ethers, higher fatty acid sucrose esters, polyglycerin fatty acid esters, higher fatty acid monoethanolamides or diethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamidoamine oxides. Of these, preferred are polyethoxylates of a secondary alcohol represented by the following formula (1):

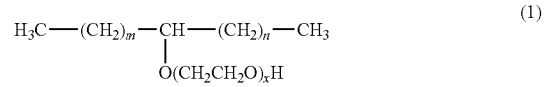

wherein, m and n stand for a number so that the sum of m and n is from 7 to 25, preferably from 7 to 20, more preferably from 9 to 11, and x is a weight average and stands for a number from 6 to 16, preferably from 6 to 12, more preferably from 8 to 10. More preferred is polyoxyethylene tridecyl ether ("Softanol 90", product of Nippon Shokubai, a compound of the formula (1) in which m+n=from 9 to 11 and x=9).

The above-described nonionic surfactants may be used either singly or in combination. The content of the non-ionic surfactant(s) in the hair dye composition of the present invention is preferably from 0.1 to 5 wt. %, more preferably from 0.5 to 3 wt. % from the viewpoints of usability and coating properties.

Examples of the anionic surfactant include alkyl benzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate ester surfactants and sulfosuccinates. Of these, sulfate surfactants are preferred, of which more preferred are sulfate surfactants that are each represented by the following formula (2):

wherein, R represents a linear or branched $C_{8-18}$ alkyl or alkenyl group, a stands for 0 or a positive integer, and M represents an alkali metal, alkaline earth metal or ammonium; is made of from 30 to 70 wt. % of a sulfate exhibiting a=0, from 14 to 27 wt. % of a sulfate exhibiting a=1, from 5 to 20 wt. % of a sulfate exhibiting a=2; and contains sulfates exhibiting a=0 to 2 in an amount of 75 wt. % or greater based on the total sulfates. Such sulfate surfactants are even more preferred for converting an injected solution into creamy and stable foams when the hair dye composition is provided in the aerosol form.

From the viewpoint of converting an injected solution into creamy and stable foams, employed are sulfate surfactants each showing the following distribution in the molar number a of ethylene oxide added in the formula (2), that is, sulfate surfactants each composed of from 30 to 70 wt. % of a sulfate exhibiting a=0, from 14 to 27 wt. % of a sulfate exhibiting a=1 and from 5 to 20 wt. % of a sulfate exhibiting a=2. Sulfate surfactants each composed of from 35 to 65 wt. % of a sulfate exhibiting a=0, from 14 to 24 wt. % of a sulfate exhibiting a=1 and from 7 to 18 wt. % of a sulfate exhibiting a=2 are preferred, with sulfate surfactants each composed of from 50 to 60 wt. % of a sulfate exhibiting a=0, from 15 to 20 wt. % of a sulfate exhibiting a=1 and from 8 to 14 wt. % of a sulfate exhibiting a=2 being more preferred. A ratio of sulfates exhibiting a=0 to 2 in the sulfate surfactant component is 75 wt. % or greater from a similar viewpoint. The ratio is preferably from 75 to 90 wt. % of all the sulfates.

In the formula (2), M represents preferably sodium or ammonium from the viewpoint of good foaming, with ammonium being more preferred from the viewpoint of foam touch.

Specific examples of the sulfate surfactants as described above include sodium polyoxyethylene (1) lauryl ether sulfate and ammonium polyoxyethylene (1) lauryl ether sulfate.

Such a sulfate surfactant can be prepared, for example, by sulfating an alcohol ethoxylate, which has been obtained by adding from 0.85 to 1.35 moles of ethylene oxide per mole of a higher alcohol ROH, by using from 0.95 to 1.0 equivalent of $SO_3$ and then neutralizing the resulting product with sodium hydroxide or ammonia.

The content of the anionic surfactant(s) in the hair dye composition of the present invention is preferably from 0.5 to 20 wt. %, more preferably from 1 to 15 wt. % from the viewpoint of providing creamy and stable foams.

Examples of the cationic surfactant include imidazoline ring-open type quaternary ammonium salts, mono(long-chain alkyl) quaternary ammonium salts, and di(long-chain alkyl) quaternary ammonium salts. Of these, preferred are mono or di(long-chain alkyl) cationic surfactants represented by the following formula (3):

wherein, $Z^1$ represents a $C_{12-28}$ alkyl group, $Z^2$ represents a methyl group or $C_{12-28}$ alkyl group, and $A^-$ represents a halide ion.

As the cationic surfactant, long-chain alkyl groups ($Z^1$ or $Z^1$ and $Z^2$ in the formula (3)) have preferably from 12 to 22 carbon atoms. Examples include lauryltrimethylammonium salts, cetyltrimethylammonium salts, stearyltrimethylammonium salts, behenyltrimethylammonium salts, dodecyl-hexadecyldimethylammonium salts and dialkyl($C_{12-18}$)dimethylammonium salts. As $A^-$ in the formula (3), chloride ions and bromide ions are preferred. Of these, di(long chain)alkyl ammonium salts are preferred.

The above-described cationic surfactants may be used either singly or in combination of two or more. The content of the cationic surfactant(s) in the hair dye composition of the present invention is preferably from 0.05 to 5 wt. %, more preferably from 0.1 to 1 wt. % from the view-points of stability and feel to the touch of the composition.

Examples of the amphoteric surfactant include imidazoline, carbobetaine, amidobetaine, sulfobetaine, hydroxysulfobetaine and amidosulfobetaine amphoteric surfactants.

The total content of these surfactants in the hair dye composition of the present invention is preferably from 0.1 to 30 wt. %, more preferably from 0.5 to 15 wt. %.

Although incorporation of a dye other than Component (A) is not necessary for the hair dye composition of the present invention, it may contain a direct dye typically employed for hair dyes.

Examples of the direct dye include acid dyes, nitro dyes, disperse dyes, basic dyes and direct dyes described in JP-A-2003-342139. Examples of the acid dyes include Blue No. 1, Violet No. 401, Black No. 401, Orange No. 205, Red No. 227, Red No. 106, Yellow No. 203, and Acid Orange 3. Examples of the nitro dyes include 2-nitroparaphenylenediamine, 2-amino-6-chloro-4-nitrophenol, 3-nitro-p-hydroxyethylaminophenol, 4-nitroorthophenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, and N,N-bis-(2-hydroxyethyl)-2-nitroparaphenylenediamine. Examples of the disperse dyes include Disperse Violet 1, Disperse Blue 1 and Disperse Black 9, while those of the basic dyes include Basic Blue 99, Basic Brown 16, Basic Brown 17, Basic Red 76, Basic Red 51, Basic Yellow 57, Basic Yellow 87 and Basic Orange 31. Of these, acid dyes are preferred, with Black No. 401 being more preferred because it can dye the hair into a black to gray color which is less reddish.

When the direct dye is added to the hair dye composition of the present invention, the content of it therein is preferably from 0.001 to 5 wt. %, more preferably from 0.01 to 3 wt. %.

The hair dye composition of the present invention may contain a linear aliphatic alcohol having from 12 to 24 carbon atoms in order to improve coating properties and foam quality of the composition. Specific examples thereof include myristyl alcohol, cetyl alcohol, stearyl alcohol, arachyl alcohol, and behenyl alcohol, with stearyl alcohol and behenyl alcohol being more preferred.

These linear aliphatic alcohols may be used either singly or in combination of two or more. Their content in the hair dye composition of the present invention is preferably from 0.1 to 10 wt. %, more preferably from 0.1 to 7 wt. %, even more preferably from 0.5 to 5 wt. %.

In the hair dye composition of the present invention, a silicone can be incorporated further from the viewpoints of texture of foams, smooth touch of foams, reduction in friction between individual hairs during shampooing or washing, and smoothness during drying. Examples of such a silicone will next be given.

(1) Dimethylpolysiloxanes

Examples include those represented by the following formula:

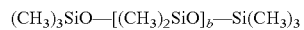

wherein, b stands for a number from 3 to 20000.

(2) Amino-Modified Silicones

Various amino-modified silicones are usable, of which those listed in the INCI dictionary (International Cosmetic Ingredient Dictionary and Handbook/USA, 10th edition) under the name of Amodimethicone, Aminoethyl aminopropyl Dimethicone or Aminopropyl Dimethicone and having an average molecular weight from about 3000 to 100000 are preferred. These amino-modified silicones are used preferably in the form of an aqueous emulsion. They are commercially available, for example, as "SM 8704C" (product of Dow Corning Toray), "DC 929" (product of Dow Corning) and "KT 1989" (product of GE Toshiba). Although no particular limitation is imposed on the N content, it is preferably from 0.01 to 1 wt. %, more preferably from 0.05 to 0.3 wt. %.

(3) Other Silicones

Examples of silicones other than the above-described ones include polyether-modified silicones, methylphenyl-polysiloxanes, fatty acid modified silicones, alcohol-modified silicones, alkoxy-modified silicones, epoxy-modified silicones, fluorine-modified silicones, cyclic silicones and alkyl-modified silicones.

Two or more silicones may be used in combination and their content in the hair dye composition of the present invention is preferably from 0.01 to 10 wt. %, more preferably from 0.05 to 6 wt. %, even more preferably from 0.3 to 3 wt. %.

To the hair dye composition of the present invention, an oil agent can be added further as another conditioning agent. Examples of the oil agent include hydrocarbons such as squalene, squalane, liquid paraffin, liquid ispraffin, and cycloparaffin; glycerides such as castor oil, cacao oil, mink oil, avocado oil and olive oil; waxes such as beeswax, spermaceti, lanolin and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearyl acid, and isopalmitic acid; unsaturated or branched higher alcohols; and other oil agents such as isostearyl glyceryl ether and polyoxypropylene butyl ether. Two or more oil agents may also be used in combination. Their content in the hair dye composition of the present invention is preferably from 0.2 to 2 wt. %, more preferably from 0.3 to 1.8 wt. %, even more preferably from 0.5 to 1.5 wt. %.

In the hair dye composition of the present invention, components typically employed for hair dyes can be incorporated in addition to the above-described components. For example, an aqueous medium, stabilizer, buffer, perfume, touch improver, chelating agent, solubilizing agent, preservative and the like can be added as needed, depending on the purpose.

The melanin precursor as Component (A) reacts with oxygen in the air under basic conditions and is converted into a melanin pigment. The hair dye composition of the present invention is therefore adjusted to a pH ranging from 8 to 11, preferably from 9 to 11.

The hair dye composition of the present invention is preferably provided in the form of an aerosol in order to maintain its dyeing power even after repeated use and improve the dyeing power. The composition in the aerosol form can be produced by filling a pressure container (aerosol can or the like) with the hair dye composition of the present invention as an aerosol stock solution, together with a propellant.

As the propellant, compressed gas and liquefied gas conventionally used for aerosol products are usable. Examples of the compressed gas include nitrogen gas, carbon di-oxide gas, and argon gas, while those of the liquefied gas include liquefied petroleum gas, volatile $C_{3-5}$ hydrocarbons and dimethyl ether. Of these, liquefied petroleum gas and dimethyl ether are preferred. Two or more propellants may be used in combination. In order to attain an adequate injection speed, the amount of the propellant(s) incorporated in the entire composition composed of the stock solution and propellant(s) is preferably from 0.5 to 20 wt. %, more preferably from 3 to 15 wt. %. In addition, it is preferred to control the internal pressure of the aerosol can after filling to fall within from 0.3 to 0.5 MPa (25° C.).

When the composition is filled in a pressure container, it is preferred to carry out clinching and deaeration simultaneously in order to reduce the air remaining inside the container. Such a deaeration operation is effective for stabilizing the content in the container. For example, the deaeration operation is preferably performed at a pressure not greater than 48 kPa.

The hair dye composition of the present invention can of course be used at room temperature, but has improved dyeing power when heat and oxygen are supplied by a drier.

EXAMPLES

Examples 1 and 2 and Comparative Example 1

An aerosol type one-part hair dye composition was obtained by preparing a stock solution of the aerosol one-part hair dye composition in accordance with the formulation shown in Table 1, filling the stock solution in an aerosol test bottle (product of Tokyo Koubunshi Corporation), clinching the bottle, and filling 0.35 MPa of a liquefied petroleum gas:dimethyl ether mixture (weight ratio=90:10) as a propellant to give a stock solution:gas ratio of 90:10 (weight ratio).

The aerosol one-part hair dye compositions thus obtained were tested and evaluated as described below and the results are shown in Table 1.

Dyeing Property ($\Delta E$):

Each of the aerosol hair dye compositions (1 g) was applied to about 1 g of a bundle of the dry white hair obtained from a Chinese woman. The resulting hair bundle was left to stand for 5 minutes at room temperature, followed by shampooing and washing with water. The above-described dyeing operation was repeated three times and then its white-hair dyeing property ($\Delta E$, Minolta CR300) and color were evaluated.

By the repetition of the above-described dyeing operations, the bundle of the white hair was dyed into a slightly reddish brown color in Example 1 and a slightly bluish dark gray color in Example 2. The hair bundle was dyed into dark gray in Comparative Example 1 and it seemed almost colorless.

Storage Stability

Each aerosol hair dye composition was filled in an aerosol container. After storage for one month at 40° C., appearance, injection performance, and hair dyeing properties of each composition were evaluated by comparing with those of the composition just after preparation. As a result, almost no change was found in the appearance, injection performance and dyeing properties.

TABLE 1

|  |  | Formulation of stock solution (wt. %) | | |
|---|---|---|---|---|
|  |  | Examples | | Comp. Ex. |
|  | Raw materials | 1 | 2 | 1 |
| (A) | 5,6-Dihydroxyindole | 0 | 0 | 0.3 |
|  | 5,6-Dihydroxyindole and 5,6-dihydroxyindole-2-carboxylic acid mixture (molar ratio: 90:10) | 0.3 | 0.3 | 0 |
| (B) | Ascorbic acid | 0.3 | 0 | 0.3 |
|  | Sodium sulfite | 0 | 0.3 | 0 |
| (C) | Monoethanolamine | 0.5 | 0.5 | 0.5 |
| Others | Hydroxypropyl xanthan gum ("Rhaball gum EX", product of Dainippon Sumitomo Pharma) | 0.3 | 0.3 | 0.3 |
|  | 95 vol. % Ethanol | 10 | 10 | 10 |
|  | Polyoxyethylene tridecyl ether ("Softanol 90", product of Nippon Shokubai) | 1.5 | 1.5 | 1.5 |

TABLE 1-continued

|  | | Formulation of stock solution (wt. %) | | |
|---|---|---|---|---|
|  | | Examples | | Comp. Ex. |
|  | Raw materials | 1 | 2 | 1 |
|  | Sodium hydroxide | q.s. | q.s. | q.s. |
|  | Citric acid | q.s. | q.s. | q.s. |
|  | Water | Balance | Balance | Balance |
|  | Total | 100 | 100 | 100 |
|  | pH | 10 | 10 | 10 |
|  | Viscosity (mPa·s) at 25° C. | 400 | 400 | 400 |
| Evaluation | Dyeing property (ΔE) after three-time dyeing operations | 40 | 40 | 40 |
|  | Storage stability | Good | Good | Good |
|  | Color tone | Brownish | Bluish | Gray |

Examples 3 and 4

An aerosol type one-part hair dye composition was obtained by preparing a stock solution of the aerosol one-part hair dye composition in accordance with the formulation shown in Table 2, filling the stock solution in an aerosol test bottle (product of Tokyo Koubunshi Corporation), clinching the bottle, and filling 0.44 MPa of LPG as a propellant to give a stock solution:propellant ratio of 90:10 (weight ratio).

The aerosol one-part hair dye compositions thus obtained were evaluated for both coating properties on a brush at low temperature (5° C.) and coating properties at high temperature (40° C.) in accordance with the following standards. In addition, the hair dye was applied to the hair at ordinary temperature (25° C.) and left to stand for 5 minutes. The hair touch was evaluated after shampooing and washing with water.

<Evaluation Method>

Low Temperature Coating Property:

The aerosol type one-part hair dye released in the form of foams, when injected at 5° C., was evaluated as "good", while the other one was evaluated as "poor".

High Temperature Coating Property:

The hair dye (1 g) was jetted from the aerosol type one-part hair dye and applied to 1 g of a white hair tress obtained from a Chinese woman. The hair which caused no dripping after left standing for 5 minutes at 40° C. was evaluated as "good", while the hair which caused dripping was evaluated as "bad".

Hair Touch After Treatment

Evaluation was made by five panelists. When the number of panelists who rated that the hair touch was good was three or more, the hair dye was evaluated as "good; when the number was one or two, the hair dye was evaluated as "fair"; and when the number was zero, the hair dye was evaluated as "poor".

TABLE 2

|  | | Formulation of stock (wt. %) | |
|---|---|---|---|
|  | Raw materials | Ex. 3 | Ex. 4 |
| (A) | 5,6-Dihydroxyindole and 5,6-dihydroxyindole-2-carboxylic acid mixture (molar ratio: 9:1) | 0.3 | 0.3 |
| (B) | Ascorbic acid | 0.3 | 0.3 |
| (C) | Monoethanolamine | 0.5 | 0.5 |
| Others | Cetyl trimethylammonium chloride | 0.1 | 0 |
|  | Dicetyl dimethylammonium chloride | 0 | 0.1 |
|  | Polyoxyethylene tridecyl ether ("Softanol 90", product of Nippon Shokubai) | 1.5 | 1.5 |
|  | Hydroxyethyl cellulose ("Cellosize HECQP52000H, product of Nagase Co.) | 0.7 | 0 |
|  | Hydroxypropyl xanthan gum ("Rhaball gum EX", product of Dainippon Sumitomo Pharma) | 0 | 0.7 |
|  | Sodium hydroxide | q.s. | q.s. |
|  | Citric acid | q.s. | q.s. |
|  | Water | Balance | Balance |
|  | Total | 100 | 100 |
|  | pH | 10 | 10 |
|  | Viscosity (mPa·s) at 25° C. | 800 | 1500 |
| Evaluation | Low-temperature coating property | Good | Good |
|  | High-temperature coating property | Good | Good |
|  | Hair touch after treatment | Good | Good |

1) Poor foaming property
2) Evaluated as "poor" due to dripping

Example 5

An aerosol type one-part hair dye composition was obtained by preparing a stock solution of the aerosol one-part hair dye composition in accordance with the formulation shown in Table 3, filling the stock solution in an aerosol test bottle (product of Tokyo Koubunshi Corporation), clinching the bottle, and filling 0.35 MPa of a liquefied petroleum gas:dimethyl ether mixture (weight ratio=88.5:11.5) as a propellant to give a stock solution:gas ratio of 90:10 (weight ratio).

As a result of hair dyeing, the aerosol type one-part hair dye composition thus prepared had its good foam quality, foaming property at low temperature, smooth conforming of an injected solution, and dyeing property.

TABLE 3

|   | Raw materials | Formulation of stock solution (wt. %) Example 5 |
|---|---|---|
| (A) | 5,6-Dihydroxyindole and 5,6-dihydroxyindole-2-carboxylic acid mixture (molar ratio: 90:10) | 0.3 |
| (B) | Ascorbic acid | 0.3 |
| (C) | Monoethanolamine | 0.5 |
| Others | Sodium lauryl sulfate ("Emal 2F-HP", product of Kao)* | 0.5 |
|   | Sodium polyoxyethylene lauryl ether sulfate ("Emal 270J, product of Kao)* | 0.5 |
|   | Polyoxyethylene tridecyl ether ("Softanol 90", product of Nippon Shokubai) | 1.5 |
|   | Hydroxyethyl cellulose ("Cellosize HECQP52000H, product of Nagase Co.) | 0.7 |
|   | Stearyl alcohol. | 0.1 |
|   | 95 vol. % Ethanol | 10 |
|   | Purified water | Balance |
|   | Total | 100 |
|   | pH | 10 |
|   | Viscosity (mPa·s) at 25° C. | 2000 |
| Evaluation | Foam quality | Good |
|   | Foaming property at low temperature | Good |
|   | Smooth conforming of hair dye | Good |
|   | Dyeing property | Good |

*Distribution of the molar number of ethylene oxide added in a mixture of them in the formula (2): a = 0: 57 wt. %, a = 1:16 wt. %, a = 2: 10 wt. %, a ≧ 3: 17 wt. %, and a = from 0 to 2: 83 wt. % in total.

Examples 6 and 7

An aerosol type one-part hair dye composition was obtained by preparing a stock solution of the aerosol one-part hair dye composition in accordance with the formulation shown in Table 4, filling the stock solution in an aerosol test bottle (product of Tokyo Koubunshi Corporation), clinching the bottle, and filling 0.5 MPa of a nitrogen gas as a propellant to give a stock solution:gas ratio of 95:5 (weight ratio).

The hair dyes thus obtained were evaluated for their dyeing properties and storage stability in accordance with the following standards.

<Evaluation Method>

Dyeing Property (ΔE):

Each of the aerosol hair dye compositions (1 g) was applied to about 1 g of a tress of the dry white hair obtained from a Chinese woman. The resulting hair tress was left to stand for 5 minutes at room temperature, followed by shampooing and washing with water. After the above-described dyeing operation was repeated three times, its white-hair dyeing property was evaluated by measuring the color of the dyed hair (Minolta CR300).

TABLE 4

|   | Raw materials | Formulation of stock solution (wt. %) Ex. 6 | Ex. 7 |
|---|---|---|---|
| (A) | 5,6-Dihydroxyindole and 5,6-dihydroxyindole-2-carboxylic acid mixture (molar ratio: 9:1) | 0.3 | 0.3 |
| (B) | Ascorbic acid | 0.3 | 0.3 |
| (C) | Monoethanolamine | 0.5 | 0.5 |
| Others | Benzyloxyethanol | 0.3 | 0 |
|   | Benzyl alcohol | 0 | 0.2 |
|   | Polyoxyethylene tridecyl ether ("Softanol 90", product of Nippon Shokubai) | 1.5 | 1.5 |
|   | Hydroxypropyl xanthan gum ("Rhaball gum EX", product of Dainippon Sumitomo Pharma) | 0.8 | 0.8 |
|   | 95 vol % Ethanol | 6 | 6 |
|   | Low-viscosity dimethicone-highly polymerized dimethicone-aminoethylaminopropyl•methylpolysiloxane copolymer mixture ("CF1046", product of Dow Corning Toray) | 0.1 | 0.1 |
|   | 1,3-Butylene glycol | 1 | 1 |
|   | 48 wt. % Aqueous solution of sodium hydroxide | q.s. | q.s. |
|   | Purified water | Balance | Balance |
|   | Total | 100 | 100 |
|   | pH | 10 | 10 |
|   | Viscosity (mPa · s) at 25° C. | 2500 | 2500 |
| Evaluation | Dyeing property (ΔE): dyeing property after three-time dyeing operations | 44 | 43 |

Examples 8 and 9

An aerosol type one-part hair dye composition was obtained by preparing a stock solution (gel form) of the aerosol one-part hair dye composition in accordance with the formulation shown in Table 5, filling the stock solution in an aerosol test bottle (product of Tokyo Koubunshi Corporation), clinching the bottle, and filling 0.5 MPa of a nitrogen gas as a propellant.

The aerosol one-part hair dye compositions thus obtained were evaluated for their dyeing properties in accordance with the following standards. The results are shown in Table 1.

Dyeing Property (ΔE):

Each of the aerosol hair dye compositions (1 g) was applied to about 1 g of a tress of the dry white hair obtained from a Chinese woman. The resulting hair tress was left to stand for 5 minutes at room temperature, followed by shampooing and washing with water. The above-described dyeing operation was repeated three times and the white-hair dyeing property (ΔE, Minolta CR300) and the color of the dyed hair were evaluated.

By the above-described dyeing operation, the tress was dyed into a gray color in Example 8, while the tress was dyed into a color ranging from brown to gray in Example 9.

TABLE 5

|   | Raw materials | Formulation of stock (wt. %) Ex. 8 | Ex. 9 |
|---|---|---|---|
| (A) | 5,6-Dihydroxyindole and 5,6-dihydroxyindole-2-carboxylic acid mixture (molar ratio: 90:10) | 0.3 | 0.3 |
| (B) | Ascorbic acid | 0.3 | 0.3 |
| (C) | Monoethanolamine | 0.5 | 0.5 |
| Others | Black No. 401 (product of Kishi Kasei) | 0.17 | 0.05 |
|  | Polyoxyethylene tridecyl ether ("Softanol 90", product of Nippon Shokubai) | 1.5 | 1.5 |
|  | Hydroxypropyl xanthan gum ("Rhaball gum EX", product of Dainippon Sumitomo Pharma) | 1.25 | 1.25 |
|  | Benzyl alcohol | 0.3 | 0.3 |
|  | Dimethicone-aminoethylaminopropyl•methylpolysiloxane co-polymer mixture ("CF1046", product of Dow Corning Toray) | 0.1 | 0.1 |
|  | Sodium hydroxide | q.s. | q.s. |
|  | Citric acid | q.s. | q.s. |
|  | Purified water | Balance | Balance |
|  | Total | 100 | 100 |
|  | pH | 9 | 9 |
|  | Viscosity (mPa · s) at 25° C. | 10000 | 10000 |
|  | Dyeing property (ΔE) after three-time dyeing operations | 48 | 45 |

What is claimed is:

1. A one-part hair dye composition comprising the following components (A) to (C):

(A): 5,6-dihydroxyindole and 5,6-dihydroxyindole-2-carboxylic acid;

(B): either one of (b1) ascorbic acid or salt thereof or (b2) sulfurous acid or salt thereof; and (C): an alkali agent, wherein the composition has a pH of from 8 to 11, wherein said hair dye composition does not contain a coupler.

2. The one-part hair dye composition according to claim 1, wherein the total content of Component (B) is from 0.01 to 5 wt. %.

3. The one-part hair dye composition according to claim 1, wherein the alkali agent is monoethanolamine and the pH of the composition is from 9 to 11.

4. The one-part hair dye composition according to claim 1, wherein a molar ratio of 5,6-dihydroxyindole to 5,6-dihydroxyindole-2-carboxylic acid in Component (A) is from 50:50 to 999:1.

5. The one-part hair dye composition according to claim 1, further comprising a nonionic surfactant.

6. The one-part hair dye composition according to claim 1, further comprising a thickening polymer.

7. The one-part hair dye composition according to claim 1, further comprising an aromatic alcohol.

8. The one-part hair dye composition according to claim 1, further comprising a sulfate surfactant which is represented by the following formula $$R-O-(C_2H_4O)_a-SO_3M \quad (2)$$

wherein, R represents a linear or branched $C_{8-18}$ alkyl or alkenyl group, the subscript "a" stands for 0 or a positive integer, and M represents an alkali metal, alkaline earth metal or ammonium; and wherein the sulfate surfactant is made of from 30 to 70 wt. % of a sulfate exhibiting a=0, from 14 to 27 wt. % of a sulfate exhibiting a=1, and from 5 to 20 wt. % of a sulfate exhibiting a=2; wherein a total amount of sulfates exhibiting a=0 to 2 accounts for 75 wt. % or greater of all sulfates.

9. The one-part hair dye composition according to claim 1, further comprising a mono- or di-(long chain alkyl) cationic surfactant represented by the following formula (2):

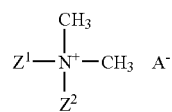

wherein, $Z^1$ represents a $C_{12-28}$ alkyl group, $Z^2$ represents a methyl or $C_{12-28}$ alkyl group, and $A^-$ represents a halide ion.

10. The one-part hair dye composition according to claim 1, further comprising a direct dye.

11. A method of controlling hair color comprising dyeing the hair with the one-part hair dye composition as claimed in any one of claims 1 to 10.

12. The composition of claim 1, wherein Component B is said (b1) ascorbic acid or salt thereof.

13. The composition of claim 1, wherein Component B is said (b2) sulfurous acid or salt thereof.

* * * * *